(12) United States Patent
Krumme

(10) Patent No.: US 10,478,145 B2
(45) Date of Patent: Nov. 19, 2019

(54) ROTARY JOINT WITH SHIELDING COMPRISING FILLED SMC AND/OR BMC MATERIALS

(71) Applicant: SCHLEIFRING GMBH, Fürstenfeldbruck (DE)

(72) Inventor: Nils Krumme, Feldafing (DE)

(73) Assignee: SCHLEIFRING GMBH, Fürstenfeldbruck (DE)

(*) Notice: Subject to any disclaimer, the term of this patent is extended or adjusted under 35 U.S.C. 154(b) by 121 days.

(21) Appl. No.: 15/480,025

(22) Filed: Apr. 5, 2017

(65) Prior Publication Data

US 2017/0215833 A1 Aug. 3, 2017

Related U.S. Application Data

(63) Continuation of application No. PCT/EP2015/073115, filed on Oct. 7, 2015.

(30) Foreign Application Priority Data

Oct. 7, 2014 (EP) .................................... 14188002

(51) Int. Cl.
*A61B 6/00* (2006.01)
*H01F 38/18* (2006.01)
*A61B 6/03* (2006.01)
*H05K 9/00* (2006.01)

(52) U.S. Cl.
CPC ............... *A61B 6/56* (2013.01); *A61B 6/035* (2013.01); *H01F 38/18* (2013.01); *H05K 9/0081* (2013.01)

(58) Field of Classification Search
CPC .................................................... A61B 6/035
See application file for complete search history.

(56) References Cited

U.S. PATENT DOCUMENTS

| 4,980,516 | A | 12/1990 | Nakagawa | |
|---|---|---|---|---|
| 5,286,318 | A | 2/1994 | Sims et al. | |
| 6,265,466 | B1 * | 7/2001 | Glatkowski | G21F 1/10 523/137 |
| 6,592,986 | B1 * | 7/2003 | Hakotani | B29C 70/025 428/295.1 |
| 2008/0139065 | A1 * | 6/2008 | Amarasekera | C08L 67/02 442/189 |
| 2010/0246645 | A1 * | 9/2010 | Fenton | G01S 19/21 375/150 |
| 2010/0276645 | A1 | 11/2010 | Aspin et al. | |
| 2014/0159499 | A1 * | 6/2014 | Dobbs | A61B 6/56 307/104 |

FOREIGN PATENT DOCUMENTS

EP 2696442 A1 2/2014

OTHER PUBLICATIONS

XP-002752405, "Sheet moulding compound," undated, Text and Image Sources, Contributors, and Licenses, 2 pages.

* cited by examiner

*Primary Examiner* — Dani Fox
(74) *Attorney, Agent, or Firm* — Quarles & Brady LLP; Yakov S. Sidorin

(57) ABSTRACT

A CT scanner with a device configured to improve the electromagnetic properties and/or the shielding of the rotation transmission devices in the CT scanner. A corresponding method for improving the electromagnetic properties and/or the shielding, of the rotation transmission devices inserted in the CT scanner.

10 Claims, 8 Drawing Sheets

ROTARY JOINT WITH SHIELDING COMPRISING FILLED SMC AND/OR BMC MATERIALS

CROSS-REFERENCE TO RELATED APPLICATIONS

This application is a continuation of International Application No. PCT/EP2015/073115 filed on Oct. 7, 2015, which designates the United States and claims priority from European Application No. 14188002.1, filed on Oct. 7, 2014.

BACKGROUND

1. Field of the Invention

The invention relates to a rotary joint with a device configured to improve the electromagnetic properties and/or the shielding of the rotating transmission devices used in the rotary joint, as well as to a method for improving the electromagnetic properties and/or the shielding of the rotating transmission devices inserted in the rotary joint.

2. Description of Relevant Art

Rotary joints in general and, specifically, sliprings are used to transmit electrical signals between components that are rotatable with respect to each other. Here, at least one brush slides on a sliding track that is rotatable against the brush. Alternatively or additionally, both the electrical transmission of supply power and the electrical transmission of control and data signals based on contactless transmission (realized with rotating transformers as well as capacitive, optical or wireless data links, such as WLAN) may be realized. During such transmission, measures must be taken to shield the signal transmission path from interference influences from outside, and to meet the legal requirements concerning the exposure to electromagnetic radiation of persons in the circumference of transmission links. For this purpose, usually shield structures made from metal are used for shielding electromagnetic radiation.

U.S. Pat. No. 4,980,516 discloses, the use of flexible conductive gaskets for the purpose of sealing metal housing structures that are often used as shielding. Such gaskets are configured to prevent the formation of slot antennas and to compensate unevenness of the housing structures in edge regions, and thus to generate mechanical tightness. An adaptation of conductive gaskets for rotary applications is not practical because these would hinder the rotational movement and cause a massive debris contamination of the machine with generated abrasive particles.

U.S. Pat. No. 5,286,318 describes a shielding structure made of non-conductive layers and conductive layers. By using this measure, the volume of materials and thus the costs for fully enclosing housing structures made of copper or aluminum are reduced while keeping mechanical characteristics substantially unchanged.

The technical implementation of such an embodiment employing conductive and non-conductive layers causes the production process to be time-consuming and thus cost-consuming. To produce such a shielding structure, the application of multiple layers of conductive material on layers of the non-conductive support material in several production steps is required.

SUMMARY

Embodiments of the present invention are directed to provide an improved electrical, magnetic, and/or electromagnetic shielding of rotary joints, sliprings and specifically rotary joints of CT scanners.

In rotary joints, energy and data are usually transmitted between rotating and stationary machine parts. In CT scanners, preferably, this transmission takes place between a rotating machine part of the gantry (which carries among others the X-ray tube and the X-ray detector and a stationary machine part of the CT scanner.

On the stationary part of the CT scanner, the first part of a rotating transformer is arranged circularly and concentrically around the passage opening of the CT, which may include a core made of a single piece or of multiple pieces, the primary coil with forward and reverse conductor and support shells for the winding. Furthermore, multiple sliprings or brushes and/or brush blocks may be arranged on the stationary part concentrically with the passage opening of the CT, and engage with sliprings or brushes and/or brush blocks, on the rotating machine part of the gantry. The rotating machine part may also comprise the second part of the rotating transformer, which is constructed to operably correspond to the first part and which comprises the secondary winding of the rotating transformer.

For data transmission, the stationary as well as the rotating part of the CT may comprise a capacitive or optical data link, which includes units for sending as well as for receiving data. The capacitive data links may also be structure to be concentric to the passage opening of the CT, and may extend around such opening. For receiving the data signals, receivers may be mounted from the stationary machine part to the rotating machine part (or in the reverse direction) with holding brackets or clips such that an appropriate minimum distance to the transmitter is realized. For radiating the data to be transmitted towards the receiver, a transmission line structure may be used that includes, for example, a strip line; an alternative transmission line structure may also be used. The receiver may comprise all electronics necessary for receiving the data and can be connected to an external device (configured to deliver or use the data) via a flexible circuit board.

Embodiments of the invention also realize shielding structures for rotary transmission systems (and, in particular, for CT scanners), which can be manufactured in a time- and cost-effective method and which provide, at the same time, high shielding efficiency together with high mechanical stability and high flexural stiffness (preferably, the degree of stiffness appropriate for protection against cracked and flying debris).

In a preferred embodiment, with CT scanners, shielding components of Sheet Molding Compound (SMC) or Bulk Molding Compound (BMC) can be arranged between or around the power- and/or data-transmitting components or assemblies.

For manufacturing the shielding components, two different composite manufacturing processes for SMC or BMC and their products, or a combination thereof (preferably together with at least one classic shielding material such as copper, aluminum, mu-metal and/or other metals such as iron and/or steel) may be used. Thus, metallic and/or ferrite materials may be incorporated as wires, fibers and/or as films.

In a particular case, when the electrically conductive material is integrated, preferably, in an inner layer of SMC/BMC, such electrically conductive material is caused to be electrically insulated from the environment. As a result, any additional insulation means can be omitted. This is particularly advantageous if the electrically conductive material is accessible at least one at one position, such that it can be contacted, for example, for grounding.

A further advantage of the embodiments is the mechanical stability of the SMC/BMC, which improves mechanical properties of the rotary joint or the slipring, respectively. Accordingly, a rotary joint may also be manufactured based on SMC/BMC, wherein the SMC/BMC serves as the base material for mechanical components.

In particular, SMC/BMC can be mounted, for example, on a rear side of a slipring module. It may also be cast in the interior of a module. It may as well be attached to or integrated into components of sliprings or rotary joints or segments thereof. Alternatively, it may be cast into a slipring module.

Preferably, the use is made of the SMC material comprising magnetically or electrically conductive particles or fibers. This is a pressed mass of thermosetting reactive resins and glass fibers for the production of fiber-reinforced plastics composites. In SMC, all necessary components are provided fully pre-mixed, ready for processing. The reinforcing fibers are provided in mat or alternatively in fabric form, with a percentage share of preferably about 10% to about 60%. The typical fiber length may be about 25 mm to about 50 mm. The mixture may also comprise inert fillers, catalysts, pigments and stabilizers, as well as release agents and thickening agents.

The production of the SMC as a mat or prepreg is preferably carried out as a continuous process. The material is covered on top and at bottom with (or sandwiched between) plastic film(s) preferably made of polyethylene or nylon to prevent adhesion to the material. The films used with SMC serve to facilitate handling during the production of the so-called SMC prepregs (2 films with plastic mixture contained there-between) for easier storage of these prepregs. The used films are preferably removed during the manufacturing process prior to casting, e.g. when inserting the material into a mold.

In a preferred manufacturing method, a first film is provided, after which a mixture of the plastics material is evenly spread on the first film. Cut fibers (preferably glass fibers) are applied to the mixture, preferably in random orientation. The mixture of plastics material may be available in a form of paste. The process of application or insertion of materials into a composite is also referred to herein as compounding. Here, the electrically and/or magnetically conductive material may be inserted as fibers and/or powder and/or granulate and/or paste and/or film and/or fabric. Thereafter, a second film is applied, and the formed sandwich material structure is rolled to a predetermined thickness. The material structure may comprise multiple layers of the materials described above.

After insertion of fibers prior to curing, or prior to installation in the rotary joint arrangement, the sandwich material structure may be cut or shaped into any desired form, or inserted into existing molds and cured therein. The curing of plastics is also referred to herein as a polymerization or polymer reaction, and can be activated, for example, by thermal radiation, pressure increase, catalysts, chemical additives, or a combination thereof. Further processing of the formed parts and/or the mats can also be performed after curing. The plastic films of polyethylene or nylon applied to the top and bottom of the sandwich material structure can be removed (in particular, before a subsequent molding process).

This method is used to enable a constant material and component quality based on a reproducible, stable process. The process parameters during processing can be adjusted and optimized for a reproducible material profile.

Thermosetting resins are vitreous polymer materials that are fixedly three-dimensionally crosslinked with chemical primary valence bonds, and represent plastics that can no more be molded after they are cured. The crosslinking is carried out either chemically (isothermally) at room temperature with the aid of catalysts, or is activated thermally (exothermically) at high temperatures. Thermosetting resins include, for example, polyester resins, vinyl ester resins, epoxy resins, melamine resins, aminoplasts, phenoplasts, polyacrylates, as well as polyurethanes.

Alternatively or in addition, embodiments of the invention may utilize the BMC materials.

Bulk Molding Compound (BMC) is a thermosetting resin mixture of various inert fillers and reinforcing fibers, as well as pigments, which forms a viscous mass. The BMC is preferably highly filled (between 10% and 30% by volume) and more preferably is reinforced with short fibers of approximately 12 mm in length. The BMC is typically processed with casting (such as injection molding, centrifugal casting).

Such BMC may also can be referred to as Dough Moulding Compound (DMC). The material is a fiber-matrix semi-finished product. It can mostly include short glass fibers and a polyester or vinyl ester resin; the use of other reinforcing fibers or resin systems (such as natural fibers) as inexpensive alternative to glass fibers, is also possible. The BMC is supplied as a shapeless mass in bags or other containers. Compared to pure resin, BMC has higher mechanical stability, stiffness and temperature limits.

The BMC is preferably processed by injection molding processes, centrifugal casting processes or is processed as prefabricated mats (prepregs), similarly to the SMC. During the fabrication process, the electrically or magnetically conductive material may be inserted as fibers and/or powder and/or granulate and/or paste and/or film and/or fabric.

The BMC has a lower fiber content compared to the SMC, for easier processing. The typical length of the fibers is also shorter (about 12 mm).

Preferably, soft magnetic materials may be used as suitable fillers for the SMC and/or BMC materials, in order to reduce the magnetization losses. In addition or alternatively to the use of glass fibers, the incorporation of carbon fibers into the material mixture is possible, in order to further increase the electrical conductivity as well as for weight reduction.

In one embodiment, the additional use of carbon nanotubes (CNT) has proven to be advantageous to reduce weight and to improve electrical conductivity of the final product. Carbon nanotubes are tubular carbon structures that are characterized by high electrical conductivity, high thermal conductivity, mechanical strength and thermal stability. As a result of such use, an increase in the number of percolation paths (that are the electrically conductive paths between the inserted conductive layers, fibers or conductive particles) is achieved.

To improve the mechanical and chemical properties, the mats or films or moldings produced of filled SMC and BMC materials can also be used as a conductive intermediate layer between other materials, such as glass fiber materials or conventional plastics, or as a composite with metals. When such specific structures are used, additional electrical insulation, or mechanical stiffening or lacquering can be omitted.

In order to carry out effective electromagnetic shielding, one should take into account the frequency of the interference to be shielded, the shield material, and the material thickness of the shield material. The effectiveness of shielding can be determined with the so-called shielding factor.

The shielding factor describes the ratio of the strength of the magnetic or electric field, reduced by the shielding, to the field strength that would occur without the shielding.

As shields show a reciprocal behavior in that they provide the same shielding effect regardless of direction—from inside to outside of a component formed by the shielding material, or vice versa), it is not relevant for the shielding effect whether the interference source is located inside or outside. For the use in CT scanners, the following basic considerations are to be made. The power to be transmitted from the rotary transformer is typically in the range of several kilowatts for supplying the X-ray tube at a frequency of preferably 20-40 kHz. Numerical simulations have demonstrated that in this frequency range the skin effect is not yet fully pronounced, and the shield thickness represents an essential factor for effective shielding. The capacitive data link, however, can transmit in megahertz or gigahertz range, in which range the shield thickness plays substantially no role due to the fully developed skin effect. In this situation, a high surface conductivity of the shield is particularly important.

The shielding of the fields generated by the rotary transformer is possible with electrically dynamic shields. Highly permeable materials such as soft iron, soft magnetic nickel, for example, may advantageously be used in electrically-dynamic shields. For low frequency fields, the shield thickness plays a crucial role, as studies have shown. For higher frequencies, the role of the thickness of the shield becomes increasingly negligible because with the increase in frequency the skin effect becomes more and more pronounced. In this case, materials with a high conductivity, such as aluminum or copper or steel, are preferably used.

It has been empirically demonstrates that the use of conductive fibers in SMC and BMC materials leads to an increase of the effective shield thickness by the formation of percolation paths. Conductive fibers are in contact with each other due to stochastic distribution of the conductive fibers in the resin or plastic matrix. In case of a desired grounding or if multiple shielding components are to be connected to each other, flexible strips of copper or aluminum, and other mechanical or electrical components as well as holding and fastening devices) may be laminated in the shield geometries manufactured during the SMC or BMC process.

The manufacturing of components from SMC and/or BMC is possible in various profile shapes. After curing, the profiles can be additionally cast with other plastics in order to increase the mechanical strength. Thus, the profiles simultaneously serve as a mold, as a result of which construction of a separate mold is no longer necessary.

The components manufactured from SMC and/or BMC materials can also be used as molds and may be cast with epoxy resin or other casting materials (which materials, in turn, may also be filled), in order to achieve a higher mechanical stability. The casting materials may be curable by UV radiation, heat or be chemically curable. The molds may have a U-shaped contour or any other contour.

The scope of the invention also includes any combination of the embodiments (disclosed in conjunction with a CT scanner) with any other rotary joint or slipring.

Another embodiment relates to a method of manufacturing a shield component of a slipring and/or rotary joint arrangement. The method comprises the steps of:
inserting at least one piece of SMC material with electrically and/or magnetically conductive material enclosed therein,
wherein the at least one SMC material comprises a first film, a second film, and between the first film and the second film a mixture of a plastic material with glass fibers as well as electrically and/or magnetically conductive material enclosed therein,
removing the first and/or the second film, and
curing the mixture.

In a further embodiment of the method, other plastic and/or metal parts are brought to the final form thereof or inserted into a corresponding cast prior to curing the material.

BRIEF DESCRIPTION OF THE DRAWINGS

In the following, the invention will be described by way of example, without limitation of the general inventive concept, on examples of embodiment and with reference to the drawings.

Figure 1:
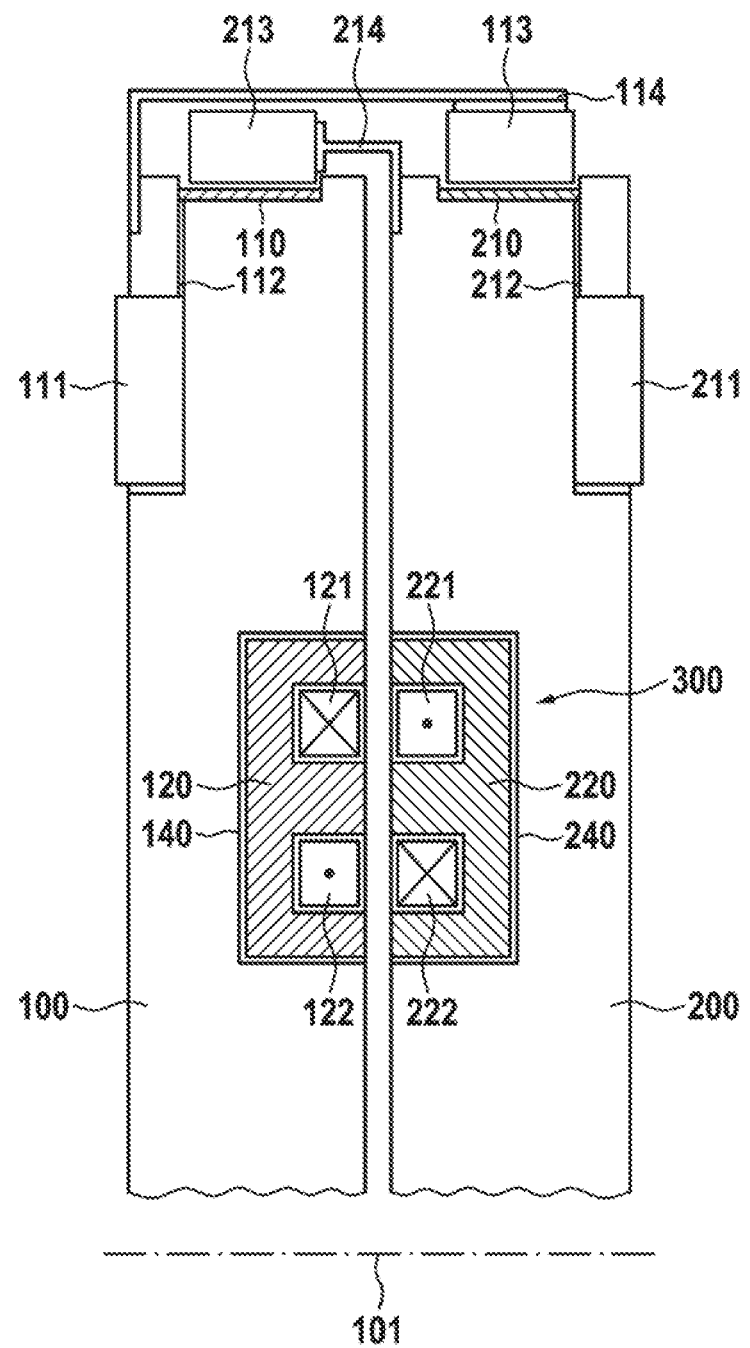
FIG. 1 shows a general structure of a rotary joint for CT scanners with data link, power transmission and shielding.

While embodiments of the invention may be varied or modified, specific embodiments thereof are shown by way of example in the drawings and are further described in detail. It should be understood, however, that the drawings and detailed description are not intended to limit the invention to any particular form disclosed, but to the contrary, the scope of intention is intended to cover all modifications, equivalents and alternatives falling within the spirit and scope of the present invention as defined by the appended claims.

DETAILED DESCRIPTION

FIG. 1 shows a contactless rotary joint in a CT scanner. It has a first machine part 100 and a second machine part 200 which are supported rotatably against each other and are rotatable about a common axis of rotation 101. The two machine parts 100, 200 being rotatable relative to each other are preferably designed similarly in shape.

Preferably, the machine parts 100, 200 can have an approximately disk-shaped contour. However, they can also be formed as a drum. Both embodiments preferably have a free inner diameter. This is generally common in CT scanners for bearing the X-rayed object. Objects may be human or animal patients or other items such as luggage or plants.

The rotary joint comprises a first contactless data link (110, 111, 112, 213, and 214), a second contactless data link (210, 211, 212, 113, and 114) and a rotary transformer 300.

The first contactless data link comprises a transmission line structure 110 for contactless transmission of the data, a transmitter 111 for feeding the data in the transmission line structure 110, a receiver 213 for receiving the data from the transmission line structure 110, and a holding bracket 214 for guiding the receiver 213 at the transmission line structure 110. The transmission line structure may be, for example, a strip line or other suitable structure.

The second contactless data link comprises a transmission line structure 210 for the contactless transmission of the data, a transmitter 211 for feeding the data in the transmission line structure 210, a receiver 113 for receiving the data from the transmission line structure 210, and a holding bracket 114 for guiding the receiver 113 at the transmission line structure 210. The holdings 112 and 212 are used for mechanical fixation of the holding bracket 114 as well as the transmission line structures 110 and 210.

For power transfer, the CT scanner is equipped with a rotary transformer 300. It has a core 120 on the first machine part 100, which may be configured E-shaped in this advantageous embodiment. A first primary-side winding 121, 122 is wound on this E-shaped core. The magnetic core 120 may consist of multiple pieces to improve mounting properties.

The secondary-side winding of the rotary transformer 221, 222 is arranged on the second machine part, which winding is also wound on an advantageously E-shaped core 220. Other core geometries are conceivable, adapted to the specific requirements. It is obvious for a person skilled in the art to configure the primary and secondary part of the rotary transformer 300 symmetrically.

In this advantageous embodiment, the machine has a data link in each direction. It is obvious that also only one data link for one direction may be provided. Preferably, CT devices comprise at least one data link from a first machine part 100 to a second machine part 200.

The body of the rotary transformer 300 may preferably be made of plastics, in order to achieve isolating properties. It may be also made of metals, and in this case serves as an electromagnetic shield with good thermal conductivity. The big disadvantage of a metal body lies in high costs and high weight.

The core of the rotary transformer 300 may at least partially be surrounded by a shield 140, 240. The shield body made of metal or of SMC or BMC materials serves as an electromagnetic shield 140, 240 between the data transmission path 110, 210 and the body of the rotary transformer 300, as well as outwardly. The shield body 140, 240 may additionally be grounded, and may as well be designed as mechanically bearing part. In case of a multi-layer structure of the shield structure 140, 240, it has to be made sure to keep the capacity of the shield structure as low as possible, in order to avoid capacitive currents.

Figure 2:
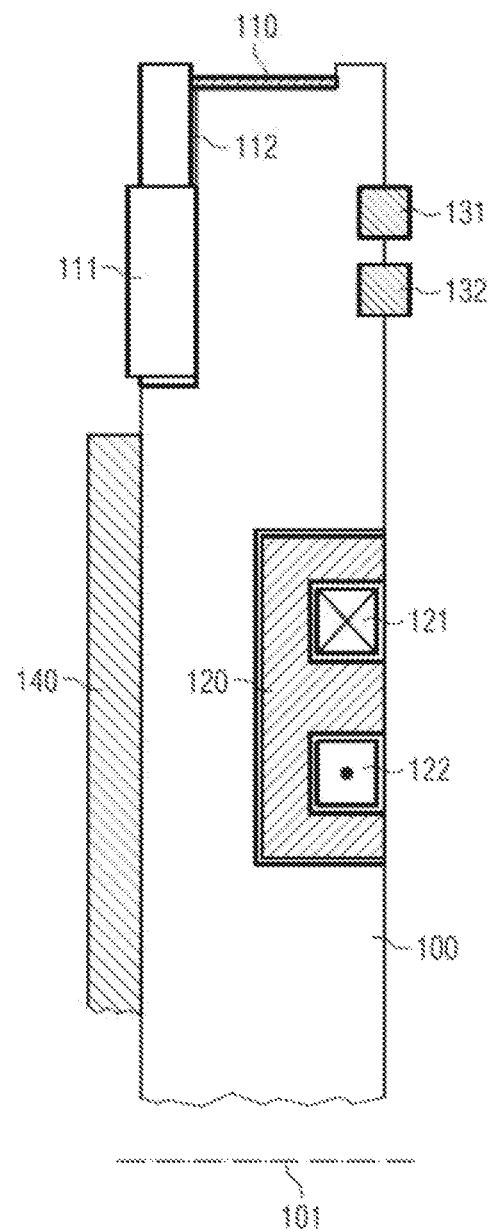
FIG. 2 shows a partial section of another rotary joint for CT scanners with a rearward mounted shielding.

FIG. 2 shows a further alternative embodiment of a first machine part 100 of a CT scanner with a conductive back plate 140 made of metal, SMC or BMC material, which serves for heat dissipation and as a shield. The shield 140 may additionally be configured grounded. Additionally, in this embodiment a first sliding track 131 and a second sliding track 132 for transmitting electrical signals and/or for providing grounding for the second opposite machine part 200 are shown.

Figure 3:
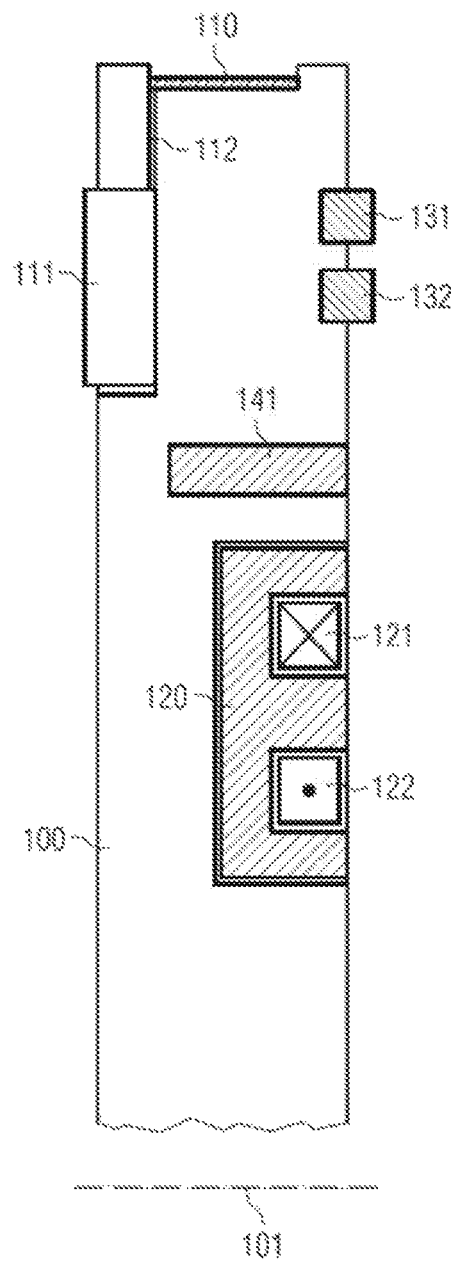
FIG. 3 shows a partial section of another rotary joint for CT scanners with a shielding arranged between data link and power transmission.

FIG. 3 shows a shielding 141 of BMC or SMC material which shields the capacitive data link from the rotary transformer and is also rotationally symmetrical about the rotational axis. Here, it is possible to integrate the shielding 141 in the first machine part 100 in the course of the production process.

Figure 4:
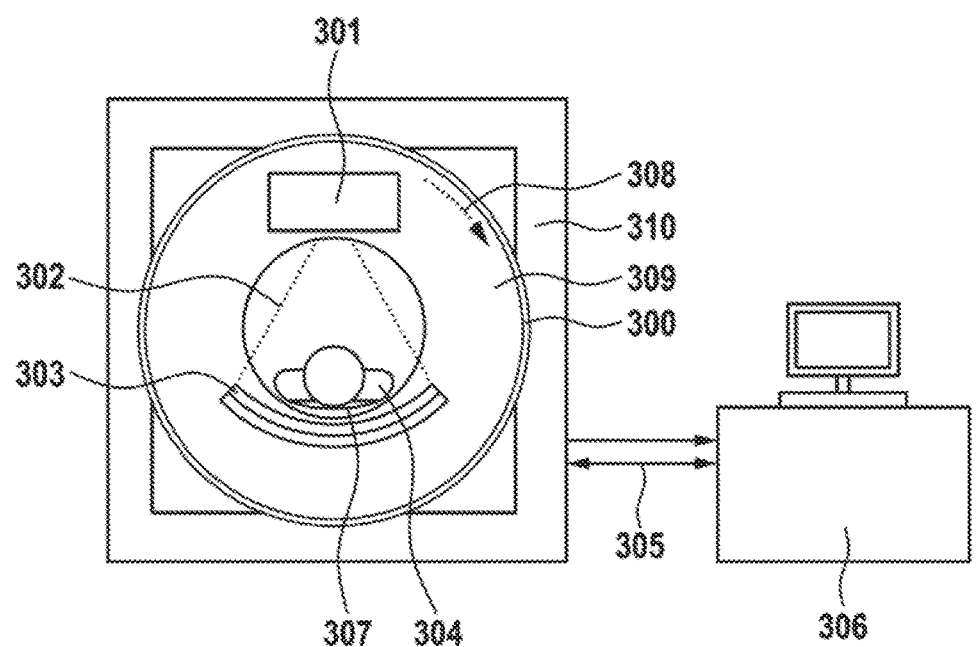
FIG. 4 shows the schematic structure of a CT scanner.

FIG. 4 shows a CT scanner in which a contactless rotary joint for data links is used. The CT scanner consists of two mechanical base parts. A fixed part 310 which serves the basis for the rotating part 309. The patient 304 is on a table 307 in a free inner diameter of the rotating machine part 309. An X-ray tube 301 and an associated X-ray detector 303 are mounted opposite to the rotating machine part, wherein the X-ray tube 302 emits the X-rays and the X-ray detector 303 receives them. The rotary transformer 300 ensures the electric power between the rotating machine part 309 and the stationary machine part. A control device 306 is used to control the CT scanner and for evaluation of the transmitted data. The communication between the CT scanner and the control device takes place via a wired data connection 305 or a wireless data connection 305.

Figure 5:
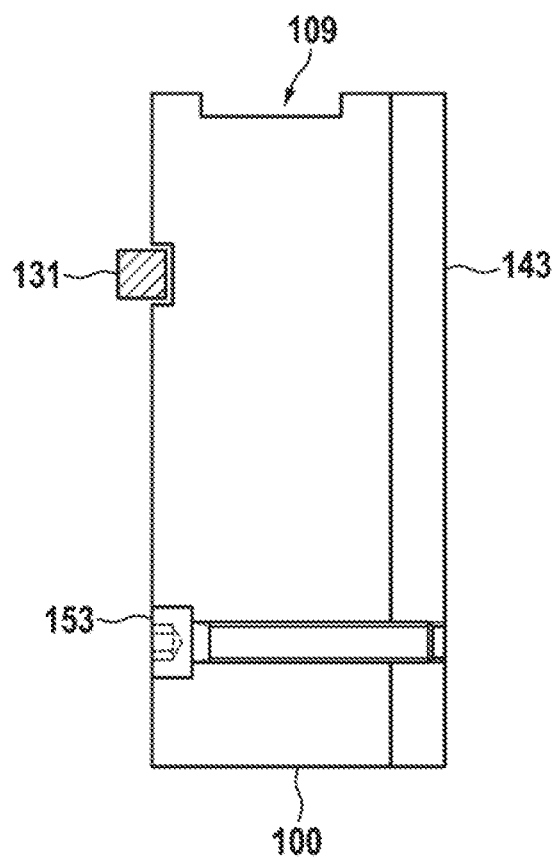
FIG. 5 shows a detail of a rotary joint for a CT scanner with mounted shield.

FIG. 5 shows the first machine part 100 of a rotary joint with a shield 143 made of SMC or BMC material mounted on one side by at least one screw connection 153. The body of the rotary joint 100 is preferably equipped with a sliding track 131 which has been molded or glued in directly during production. Furthermore, a groove 109 for receiving the transmission line structure for a capacitive data link is provided.

The shield 143 may also be glued. The complete slipring is mounted in the device by means of at least one screw connection 153.

Figure 6:
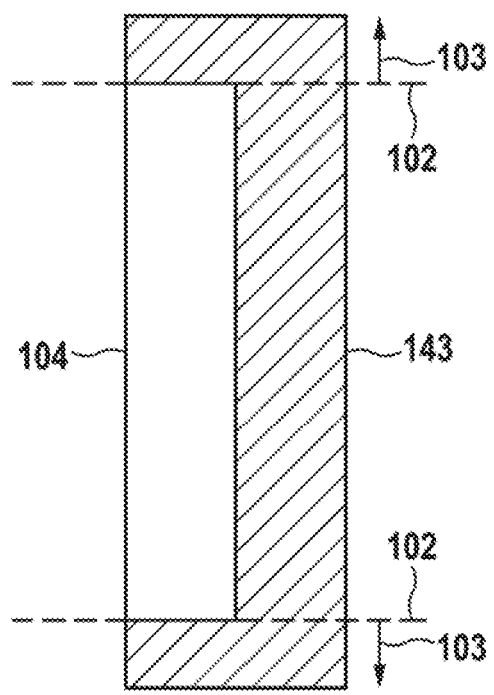
FIG. 6 shows a shell of SMC or BMC for casting and subsequent processing.

FIG. 6 shows a shield structure at the beginning of manufacturing. The U-shaped shell of BMC or SMC material, which will act as a shield 143, is filled with casting material 104, preferably made of non-conductive plastics, such as for example polyurethane or epoxy resins, in order to provide a higher mechanical strength to the entire shield structure. The casting material may additionally be filled with fillers. The U-shaped shell therefore serves as a mold. After casting with plastics or epoxy resins, the side edges can be cut to the required final size at the cutting lines 102, wherein the cutting edges 102 can be moved in direction 103.

Figure 7:
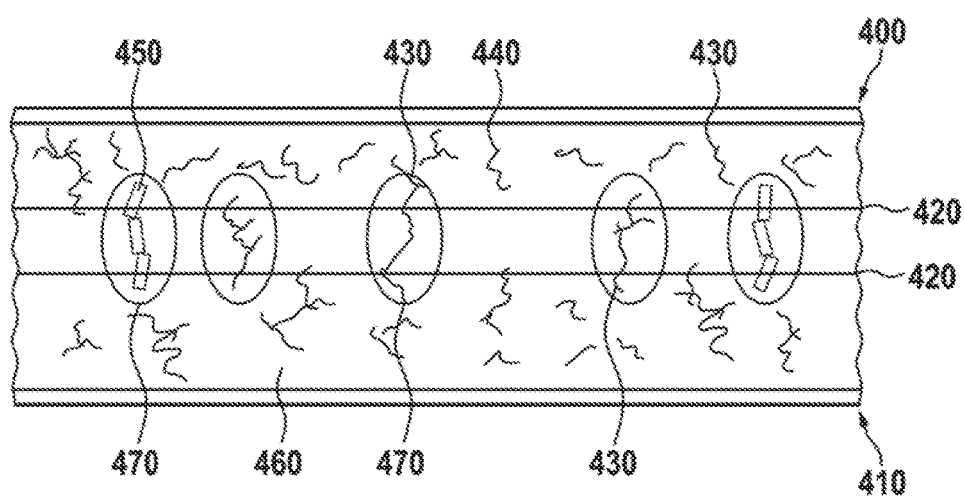
FIG. 7 shows filled SMC material in conjunction with conductive layers.

FIG. 7 shows a composite of SMC material with a first film 400 and second film 410 and conductive layers 420 in a casting compound 460. The casting compound is filled with conductive fibers 430, carbon nanotubes 450 and glass fibers 440, for increasing the mechanical stability. The carbon nanotubes 450 as well as the conductive fibers 430 form percolation paths 470 (electrically conductive paths) between the conductive layers 420 at stochastically distributed locations.

Figure 8:
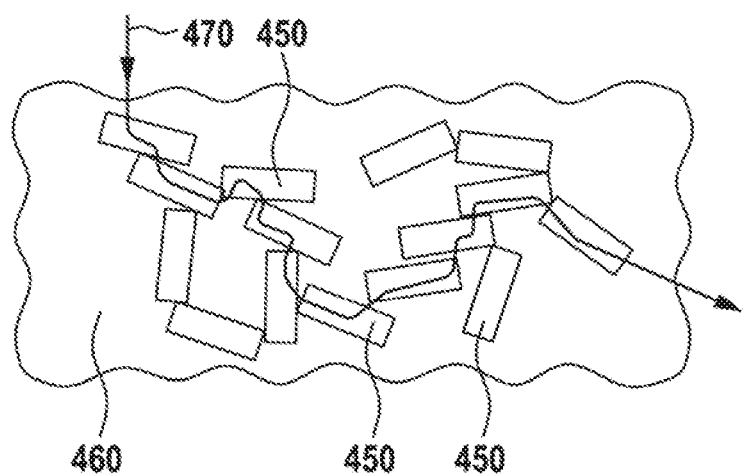
FIG. 8 shows a filled SMC or BMC material with carbon nanotubes.

FIG. 8 shows a detail of an SMC or BMC materials 460 filled with carbon nanotubes 450. One or more percolation paths 470 are generated by the statistical contact of the carbon nanotubes. Thereby, a power transfer inside the material and thus a shielding is effected.

It will be appreciated to those skilled in the art having the benefit of this disclosure that this invention is believed to provide a shielding for a rotary joint or a rotary joint comprising a shielding. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 first machine part
101 rotation axis 102 cutting edge
103 displacement direction
104 casting material
109 groove
110 transmission line structure
111 transmitter
112 holding device
113 receiver
114 holding bracket
120 core of the rotary transformer
121 winding
122 winding
131 first sliding track
132 second sliding track
140 shield
141 shield
143 shield
153 screw connection
200 second machine part
210 transmission line structure
211 second transmitter
212 holding device
213 receiver
214 holding bracket
220 core of the rotary transformer
221 winding
222 winding
240 shield
300 rotary transformer
301 X-ray tube
302 X-ray
303 X-ray detector
304 patient
305 data link
306 control panel
307 patient table
308 rotation direction
309 rotating machine part
310 stationary machine part
400 first film
410 second film
420 conductive intermediate layer
430 conductive fiber
440 glass fiber
450 carbon nanotubes
460 mass of SMC or BMC material
470 percolation path

The invention claimed is:

1. A rotary joint comprising:
   a first contactless data link of a rotary joint, said first contactless data link including
      a first transmission line structure,
      a second transmitter configured to feed a first signal representing first data into the first transmission line structure,
      a first receiver configured to receive the first signal from the first transmission line structure, and
      a first holding bracket configured to guide the first receiver at the first transmission line structure;
   at least one shielding component disposed around at least the first contactless data link and made of a sheet molding compound (SMC) material configured as a layer that is made of a mix of a) thermosetting reactive resins and b) reinforcing fibers, and configured in a mat form or in a fabric form,
   and
      first and second plastic films sandwiching the at least one shielding component therebetween, the first and second plastic films configured to prevent adhesion of an external body to said mat or fabric,
      wherein the SMC material encloses at least one of an electrically conductive material and a magnetically conductive material.

2. A rotary joint according to claim 1, wherein said at least one shielding component comprises a mixture of a plastic material and glass fibers.

3. A rotary joint according to claim 2, wherein the plastic material is uncured.

4. A rotary joint according to claim 1, further comprising a plastic material, wherein the plastic material comprises carbon nanotubes as fillers.

5. A rotary joint according to claim 1, further comprising a plastic material, wherein the at least one of the electrically conductive material and the magnetically conductive material comprises at least one metal in at least one of the following forms: a granulate, a paste, and a fabric.

6. A rotary joint according to claim 5, wherein the at least one metal present in a form of a filler comprises at least one of ferrite, copper, aluminum, mu-metal, iron, and steel.

7. A rotary joint according to claim 1, wherein said at least one shielding component constitutes a casting mold and a casting compound, said casting compound being inside the casting mold.

8. A CT scanner comprising a rotary joint according to claim 1, and further comprising at least a gantry, an x-ray source, and an x-ray detector.

9. A rotary joint according to claim 1, wherein the SMC material additionally encloses a flexible strip of an electrically-conductive material that is dimensioned to ground the at least one shielding component during operation of the rotary joint.

10. A rotary joint according to claim 1, further comprising a second contactless data link of the rotary joint, the second contactless data link including
   a second transmission line structure,
   a second transmitter configured to feed a second signal representing second data into the second transmission line structure,
   a second receiver configured to receive the second signal from the second transmission line structure, and
   a second holding bracket configured to guide the second receiver at the second transmission line structure;
   wherein the at least one shielding component is disposed around the second contactless data link.

* * * * *